United States Patent
Woo (10) Patent No.: US 9,014,777 B2
(45) Date of Patent: Apr. 21, 2015

(54) DETACHABLE BIOLOGICAL SIGNAL MEASURING PAD AND BIOLOGICAL SIGNAL MEASURING APPARATUS USING THE SAME

(75) Inventor: Sung Hun Woo, Suwon (KR)

(73) Assignee: Umedix Corporation Limited, Seongnam, Gyeonggi-do (KR)

(*) Notice: Subject to any disclaimer, the term of this patent is extended or adjusted under 35 U.S.C. 154(b) by 134 days.

(21) Appl. No.: 13/810,094

(22) PCT Filed: Jul. 22, 2011

(86) PCT No.: PCT/KR2011/005437
§ 371 (c)(1),
(2), (4) Date: Jan. 14, 2013

(87) PCT Pub. No.: WO2012/011780
PCT Pub. Date: Jan. 26, 2012

(65) Prior Publication Data
US 2013/0116534 A1 May 9, 2013

(30) Foreign Application Priority Data

Jul. 23, 2010 (KR) .................. 10-2010-0071180
Jul. 23, 2010 (KR) .................. 10-2010-0071181

(51) Int. Cl.
| | |
|---|---|
| A61B 5/04 | (2006.01) |
| A61B 5/0408 | (2006.01) |
| A61B 5/0478 | (2006.01) |
| A61B 5/0492 | (2006.01) |
| A61B 5/00 | (2006.01) |
| A61B 5/01 | (2006.01) |
| A61B 5/024 | (2006.01) |
| A61B 5/0205 | (2006.01) |

(Continued)

(52) U.S. Cl.
CPC ............. *A61B 5/6833* (2013.01); *A61B 5/0002* (2013.01); *A61B 5/01* (2013.01); *A61B 5/02438* (2013.01); *A61B 5/0205* (2013.01); *A61B 5/02055* (2013.01); *A61B 5/0245* (2013.01); *A61B 5/04* (2013.01); *A61B 5/04087* (2013.01); *A61B 5/0478* (2013.01); *A61B 5/0492* (2013.01); *A61B 5/14532* (2013.01); *A61B 5/7203* (2013.01); *A61B 5/7225* (2013.01)

(58) Field of Classification Search
USPC ........................................ 600/391–393, 509
See application file for complete search history.

(56) References Cited

U.S. PATENT DOCUMENTS

| | | | | |
|---|---|---|---|---|
| 5,511,553 | A | * | 4/1996 | Segalowitz ................... 600/508 |
| 6,117,077 | A | * | 9/2000 | Del Mar et al. ............... 600/301 |

(Continued)

FOREIGN PATENT DOCUMENTS

| | | |
|---|---|---|
| CN | 101534706 A | 9/2009 |
| EP | 2000085 A2 | 12/2008 |

(Continued)

*Primary Examiner* — Lee S Cohen
(74) *Attorney, Agent, or Firm* — Sherr & Jiang, PLLC (57) ABSTRACT

Disclosed is a detachable biological signal measuring pad that may conveniently measure biological signals such as a pulse or body temperature. The biological signal measuring pad includes an adhesive pad main body detachably adhered to a body, a biological signal detecting electrode provided on an adhesive surface of the main body adhered to the body, and a module chip including a memory card mounted on the main body so as to be connected with the electrode and storing biological signals measured in the electrode, and provided on a surface opposite to the adhesive surface.

9 Claims, 8 Drawing Sheets

(51) Int. Cl.
*A61B 5/0245* (2006.01)
*A61B 5/145* (2006.01)

(56) References Cited

U.S. PATENT DOCUMENTS

| | | | |
|---|---|---|---|
| 6,238,338 B1 * | 5/2001 | DeLuca et al. | 600/300 |
| 6,643,541 B2 * | 11/2003 | Mok et al. | 600/546 |
| 6,856,832 B1 * | 2/2005 | Matsumura et al. | 600/523 |
| 8,214,009 B2 * | 7/2012 | Shin et al. | 600/391 |
| 8,332,009 B2 * | 12/2012 | McLaughlin et al. | 600/372 |
| 2005/0131288 A1 * | 6/2005 | Turner et al. | 600/391 |
| 2006/0155183 A1 | 7/2006 | Kroecker et al. | |
| 2007/0208232 A1 | 9/2007 | Kovacs | |

FOREIGN PATENT DOCUMENTS

| | | | |
|---|---|---|---|
| GB | 2149918 | * | 6/1985 |
| JP | 2004-529709 A | | 9/2004 |
| JP | 2007-209428 A | | 8/2007 |
| JP | 2007-296266 A | | 11/2007 |

* cited by examiner

DETACHABLE BIOLOGICAL SIGNAL MEASURING PAD AND BIOLOGICAL SIGNAL MEASURING APPARATUS USING THE SAME

CROSS REFERENCE TO PRIOR APPLICATIONS

This application is a National Stage Patent Application of PCT International Patent Application No. PCT/KR2011/005437 (filed on Jul. 22, 2011) under 35 U.S.C. §371, which claims priority to Korean Patent Application Nos. 10-2010-0071180 (filed on Jul. 23, 2010) and 10-2010-0071181 (filed on Jul. 23, 2010), which are all hereby incorporated by reference in their entirety.

TECHNICAL FIELD

The present invention relates to a detachable biological signal measuring pad and a biological signal measuring apparatus using the same, and more particularly, to a detachable biological signal measuring pad that may greatly improve portability and ease of use, and a biological signal measuring apparatus using the same.

BACKGROUND ART

With the advent of the well-being age in recent years, concern about health is gradually growing, and especially early identification and management of the health status of individuals has been known as the most important issue to maintain a healthy life. In particular, well monitoring of biological signals from the body such as pulse or body temperature with respect to health care groups such as the elderly or the chronically ill, is to prevent misfortune such as rapid degradation of the quality of life, and therefore the importance of good understanding of one's health status has been further emphasized. However, as society is gradually aging and population of the elderly is increasing, the number of the chronically ill is increasing due to the westernization of eating habits, whereas an environment to identify and manage biological signals associated with the health of the individuals has not been significantly improved. That is, the number of persons of the health care group whose health status needs to be particularly well-managed is increasing, but an environment to frequently measure the health status of each individual is not actually established. Typically, because a person who wishes to identify their health status has to use examination equipment provided from a medical institution, it is difficult to frequently identify his/her health status, and therefore persons of the health care group having severe ups and downs in their health status have low efficiency. In recent years, home inspection equipment capable of measuring biological signals at home such as an electrocardiogram has been released, but is generally too big and heavy to move, and only measured results are obtainable, and therefore, it is difficult for a user to directly determine which action he/she should take from the measured results unless the user goes again to a medical facility to enquire and seek advice. Accordingly, there is a demand for a new type of system for measuring biological signals that may be more easily portable, and improve utilization of measured results.

DISCLOSURE

Technical Problem

The present invention is directed to a detachable biological signal measuring pad which may be more easily portable and improve utilization of measured results, and a biological signal measuring apparatus using the same.

Technical Solution

According to an aspect of the present invention, there is provided a detachable biological signal measuring pad, including: an adhesive pad main body detachably adhered to a body; a biological signal detecting electrode provided on an adhesive surface of the main body adhered to the body; and a module chip including a memory card mounted on the main body so as to be connected with the electrode and storing biological signals measured in the electrode, and provided on a surface opposite to the adhesive surface.

According to another aspect of the present invention, there is provided a biological signal measuring apparatus including: a detachable biological signal measuring pad including an adhesive pad main body detachably adhered to a body, a biological signal detecting electrode provided on an adhesive surface of the main body adhered to the body, and a module chip including a memory card mounted on the main body so as to be connected with the electrode and storing biological signals measured in the electrode; and an analysis device receiving and analyzing the biological signals stored in the memory card.

According to still another aspect of the present invention, there is provided a detachable biological signal measuring pad including: a pad main body detachably adhered to a body; a biological signal detecting electrode provided on an adhesive surface of the main body adhered to the body; a card module chip including a memory card for storing the biological signals measured in the electrode and a power supply unit for supplying power mounted therein, and provided on a surface opposite to the adhesive surface so as to be physically connected with the electrode; a connecting pad provided between the electrode of the main body and the card module chip, and including a connecting means for physically connecting the module chip and the electrode, the connecting means including a connecting pin protruding from the card module chip and a plug groove connected with the electrode and formed on the connecting pad so as to receive the connecting pin; and a sensing module provided on the connecting pad so as to be electrically connected with the plug groove of the connecting means, and including a sensing unit for amplifying the biological signals from the electrode transmitted through the plug groove and removing noise.

According to yet another aspect of the present invention, there is provided a biological signal measuring apparatus including: a system-on-chip biological signal measuring pad including a card module chip in which a memory card is mounted; and an analysis device receiving and analyzing the biological signals stored in the memory card, wherein the system-on-chip biological signal measuring pad includes an adhesive pad main body detachably adhered to a body, a biological signal detecting electrode provided on an adhesive surface of the main body adhered to the body, a card module chip including a memory card for storing the biological signals measured in the electrode and a power supply unit for supplying power mounted therein, and provided on a surface opposite to the adhesive surface so as to be physically connected with the electrode, and a connecting pad provided between the electrode of the main body and the card module chip, and including a connecting means for physically connecting the card module chip and the electrode and a sensing module chip provided on the connecting pad so as to be electrically connected with a plug groove, wherein the connecting means includes a connecting pin protruding from the card module chip and the plug groove formed on the connecting pad so as to receive the connecting pin, and wherein the sensing module chip includes a sensing unit for amplifying the biological signals from the electrode transmitted through the plug groove and removing noise.

Advantageous Effects

As described above, according to the embodiments of the present invention, the detachable biological signal measuring pad may be easily carried by a user, and therefore the health status of the user may be conveniently measured anytime and anywhere. In addition, the detachable biological signal measuring pad may be communicated with the analysis device by loading the detachable memory card in the analysis device or using wireless communication, and therefore the measured results are rapidly utilized. As a result, rapid measuring and utilization of the biological signals are achieved to thereby realize a healthy society.

In addition, in the detachable biological signal measuring pad, the sensing module chip and the card module chip are separately implemented, and therefore the detachable biological signal measuring pad may be attached and detached according to a variety of applications. As a result, the size of the detachable biological signal measuring pad may be further reduced, and power consumption may be further reduced. In particular, the detachable biological signal measuring pad may be replaced in accordance with a variety of biological signals such as ECG waveforms, EEG waveforms, EMG waveforms, pulse waveforms, body temperature, blood sugar, and the like, and simultaneously measure the above-described biological signals.

MODE FOR INVENTION

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Hereinafter, preferred embodiments of the present invention will be described in detail with reference to the accompanying drawings.

Figure 1:
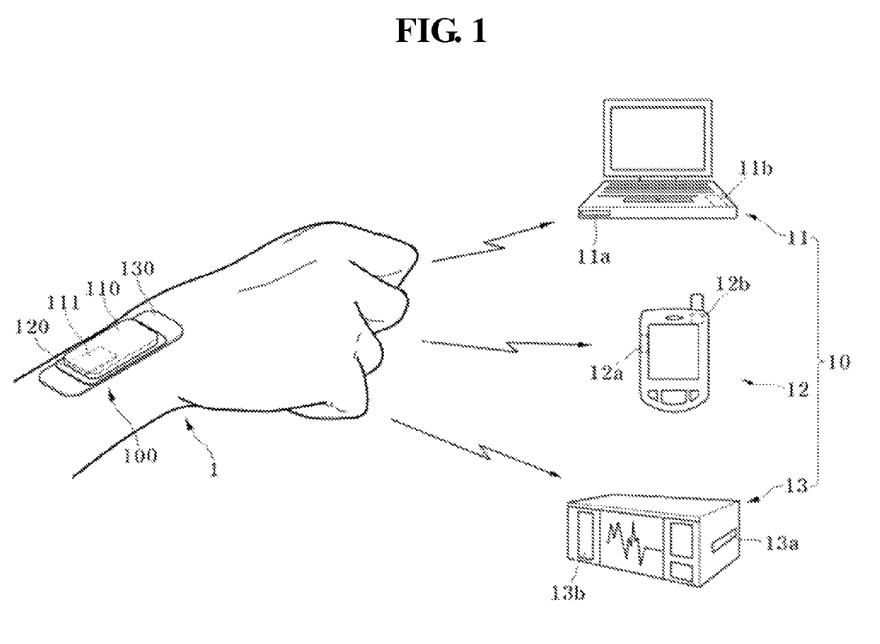
FIG. 1 is a drawing showing a configuration of a biological signal measuring apparatus including a detachable biological signal measuring pad according to a first embodiment of the present invention.

FIG. 1 is a drawing schematically showing a system configuration of a biological signal measuring apparatus according to a first embodiment of the present invention. As shown in FIG. 1, the biological signal measuring apparatus according to the present invention includes a detachable biological signal measuring pad 100 that may be attached and detached to and from a user's body such as a wrist 1, like a band-aid, and an analysis device 10 that receives and analyzes biological signals measured in the measuring pad 100. That is, when the biological signal measuring pad 100 is attached to a user's skin, biological signals such as a pulse or body temperature may be measured and recorded in a memory card 111 mounted in the pad 100, the recorded information may be analyzed which is transmitted to a mobile phone 12 or a dedicated terminal 13 such as a computer 11 of a medical institution or a smart phone, and then the analyzed information may be provided to the user as useful information. Here, as an example, a case in which the measuring pad 100 is attached to the wrist 1 has been described, but the measuring pad 100 may be attached to the chest or the head, as necessary, and the measured biological signals encompass electrocardiogram (ECG) waveforms, electro-encephalogram (EEG) waveforms, electromyogram (EMG) waveforms, pulse waveforms, a body temperature, a blood sugar, and the like.

Accordingly, a user attaches the biological signal measuring pad 100 to an appropriate body region so as to measure biological signals, as necessary, while carrying the biological signal measuring pad 100 like a band-aid, and transmits the measured biological signals to the analysis device 10 to check his/her own health status and required measures. As a method of transmitting the biological signals to the analysis device 10, both a method in which the memory card 111 mounted on the measuring pad 100 is pulled and directly inserted into card slots 11a, 12a, and 13a of the analysis device 10 to thereby load measured data, and a method in which the biological signals are transmitted to the communication modules 11b, 12b, and 13b of the analysis device 10 in a wireless manner using a personal area network (PAN), may be used.

Figure 2:
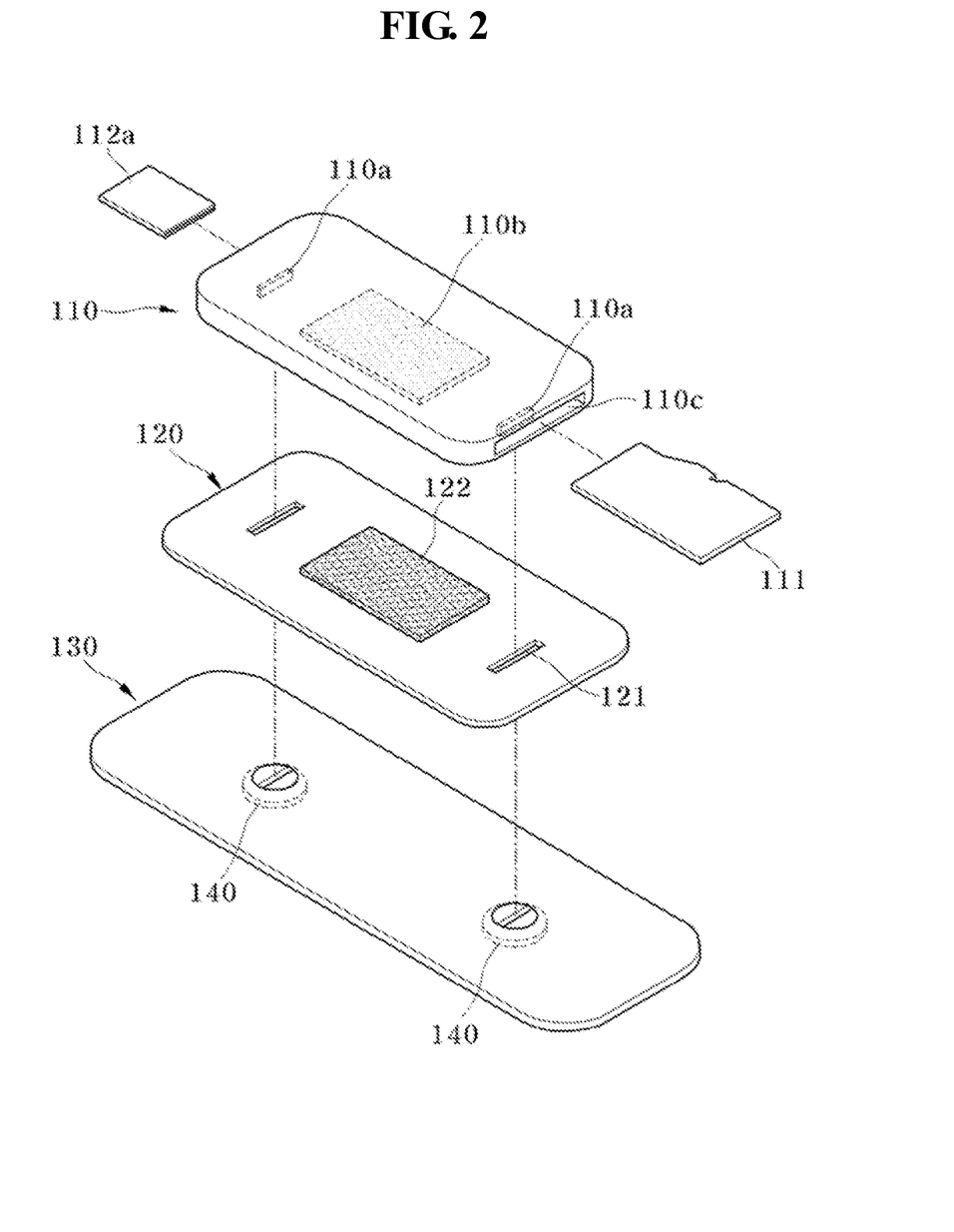
FIG. 2 is an exploded perspective view showing the detachable biological signal measuring pad shown in FIG. 1.
Figure 3:
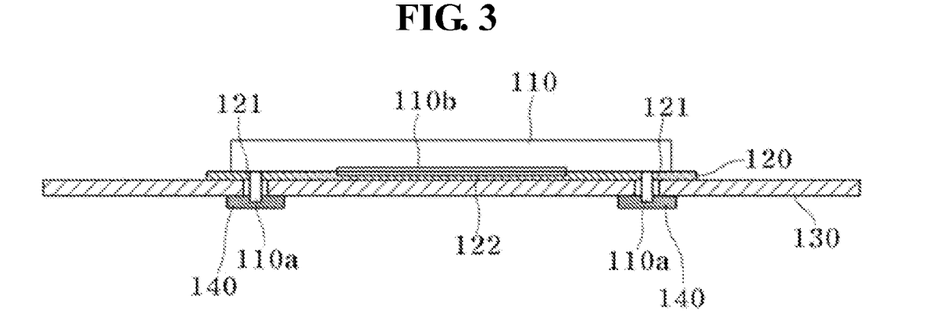
FIG. 3 is a cross-sectional view showing a coupling state of FIG. 2.
Figure 4:
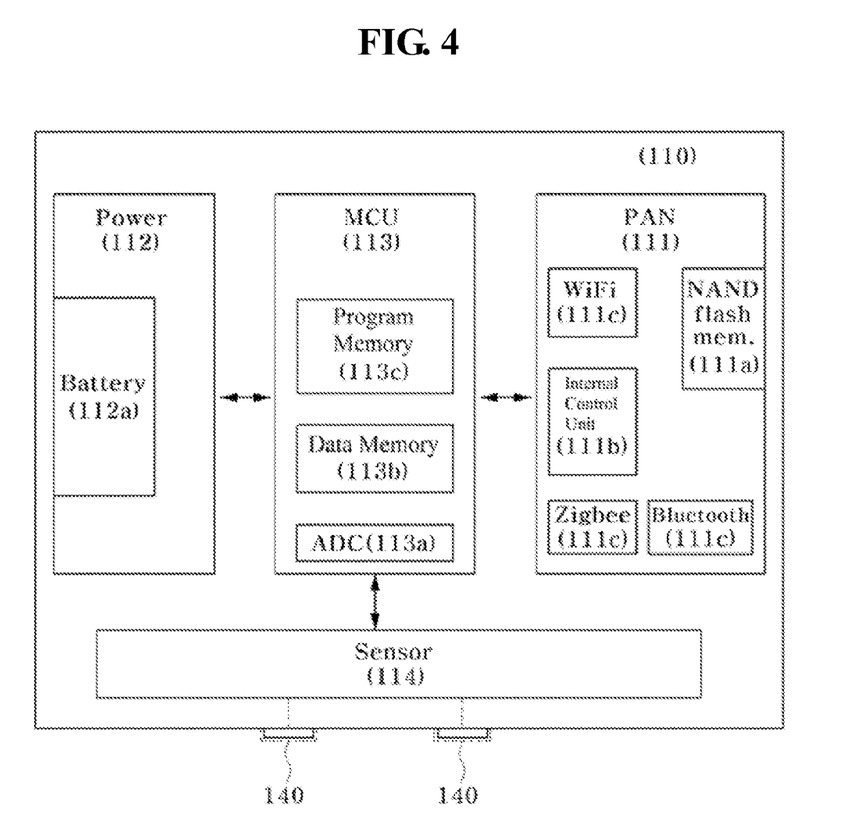
FIG. 4 is a drawing showing an internal configuration of a module chip of the detachable biological signal measuring pad shown in FIG. 2.

Hereinafter, the biological signal measuring pad 100 according to an embodiment of the present invention which is configured so as to implement the above-described function will be described in detail. FIGS. 2 and 3 are drawings respectively showing an exploded state and a coupling state of a structure of the biological signal measuring pad 100, and FIG. 4 is a drawing showing an internal structure of the module chip 110 that is a core component.

First, referring to FIGS. 2 and 3, the biological signal measuring pad 100 includes an adhesive pad main body 130 capable of attaching to skin, a module chip 110 in which a memory card 111 and a battery 112a are detachably inserted through a slot 110c, and a connecting pad 120 interposed between the pad main body 130 and the module chip 110.

A bottom surface of the pad main body 130 is an adhesive surface attached to skin, and a pair of electrodes 140 for measuring biological signals is mounted on the adhesive surface. That is, when attaching the measuring pad 100 to skin, the pair of electrodes 140 are brought into contact with the skin, and receive biological signals such as a pulse or body temperature as electrical signals. Next, the pair of electrodes 140 are connected with a connecting pin 110a of the module chip 110 through a connecting means provided in a connecting pad 120. Accordingly, the biological signals received through the electrode 140 are transmitted to the module chip through the connecting pin 110a. A process of processing signals in the module chip 110 will be described below with reference to FIG. 4. A reference numeral 121 indicates a plug groove composed of the connecting means for connecting the electrode 140 and the module chip 110 together with the connecting pin 110a. That is, the connecting pin 110a of the module chip 110 is connected to the electrode 140 provided on the pad main body 130 through the plug groove 121 of the connecting pad 120. Preferably, adhesive members 110b and 122 adhered to each other are provided above the connecting pad 120 and below the module chip 110. Obviously, a binding force through forcible coupling between the connecting pin 110a and the electrode 140 is maintained, but the adhesive members 110b and 122 more firmly fix the module chip 110. The pad main body 130 and the connecting pad 120 are coupled with each other through an adhesive.

Next, an internal configuration of the module chip 110 will be described with reference to FIG. 4.

As shown in FIG. 4, the module chip 110 includes a sensing unit 114 that amplifies the biological signals from the electrode 140 and removes noise, a microcomputer unit 113 that controls the module chip 110 by processing the biological signals input from the sensing unit 114 and storing the processed biological signals in the memory card 111, and a power supply unit 112 that supplies power to the module chip 110. As described in FIG. 2, the memory card 111 and the battery 112a are attached and detached to and from the module chip 110 through the slot 110c, the battery 112a inserted into the module chip 110 is mounted in the power supply unit 112, and the memory card 111 is mounted so as to be connected with the microcomputer unit 113. The microcomputer unit 113 includes an AD converter 113a for converting the biological signals received through the sensing unit 114 from analog signals to digital signals, a data memory 113b for storing the biological signals converted into the digital signals, and a program memory 113c for storing a program controlling the module chip 110. Accordingly, the analog biological signals received from the sensing unit 114 in accordance with the program stored in the program memory 113c are converted into digital signals through the AD converter 113a, stored in the data memory 113b, transmitted to the memory card 111, and then stored in the memory unit 111a. The memory card 111 includes a memory unit 111a for storing the measured digital signals, a communication unit 111c for transmitting the stored biological signals to the outside, and an internal control unit for controlling storage and transmission in accordance with a control of the module chip 110. The internal control unit 111b may compress or encrypt data. The communication unit 111c may include zigbee, Bluetooth, WiFi, or the like, as PAN. Accordingly, the biological signal data stored in the memory unit 111a may be transmitted by communicating with the communication modules 11b, 12b, and 13b of the analysis device 10 through the communication unit 111c as described above. Alternatively, the biological signal data may be transmitted in such a manner that the memory card 111 itself is pulled out from the module chip 110, and then is loaded which is inserted into the card slots 11a, 12a, and 13a of the analysis device 10.

The biological signal measuring apparatus described as above may be utilized as follows.

As shown in FIG. 1, a user attaches the biological signal measuring pad 100 to an appropriate body region when wishing to measure his own health status while carrying the biological signal measuring pad 100. Here, a case in which a user attaches the pad 100 to his own wrist 1 to measure a pulse waveform is assumed. Obviously, in this instance, the memory card 111 for data storage and communication and the battery 112a that is a power source, should be mounted in the module chip 110. Before attaching the pad 100 to the body, a conductive gel may be attached to the electrode 140. In this manner, when attaching the pad 100 to the wrist 1, analog biological signals such as pulse waveforms are measured through the electrode 140, and the measured analog biological signals are transmitted to the module chip 110 through the connecting pin 110a connected with the electrode 140. The analog signals transmitted into the module chip 110 are amplified in the sensing unit 114, converted into digital signals in the AD converter 113a, and then stored in the data memory 113b and the memory unit 111a of the memory card 111. In this state, when the user wishes to check analyzed results by immediately transmitting the measured biological signals to the analysis device 10, data may be transmitted in such a manner that the communication unit 111c is connected with the communication modules 11a, 12a, and 13a of the analysis device 10 in a wireless manner. Although not shown in the drawings, a transmission button may be provided on one side of the module chip 110, and the internal control unit 111b operates the communication unit 111c to thereby initiate wireless communication when a corresponding button is pushed by a user. Alternatively, a user pulls the memory card 111 out from the module chip 110, and directly mounts the memory card 111 in the analysis device 10 to thereby transmit data.

The analysis device 10 analyzes the transmitted biological signals, and informs diagnostic results suitable for the analyzed signals. When the pulse waveform measured by the user is in a normal range, the analysis device 10 informs a corresponding diagnostic result as normal, and when the pulse waveform is in an abnormal range such as bradycardia or pyknocardia, the analysis device 10 informs required measures such as recommending diagnosis of a corresponding health status and consultation with experts, or the like. Then, the user may well manage his health status by appropriately performing corresponding measures.

Therefore, by utilizing the detachable biological signal measuring pad and apparatus, a user may conveniently measure his own health status anytime and anywhere, and communicate with the analysis device by loading the detachable memory card in the analysis device or using wireless communication, and therefore the measured results are rapidly utilized. As a result, rapid measuring and utilization of the biological signals are achieved to thereby realize a healthy society.

Figure 5:
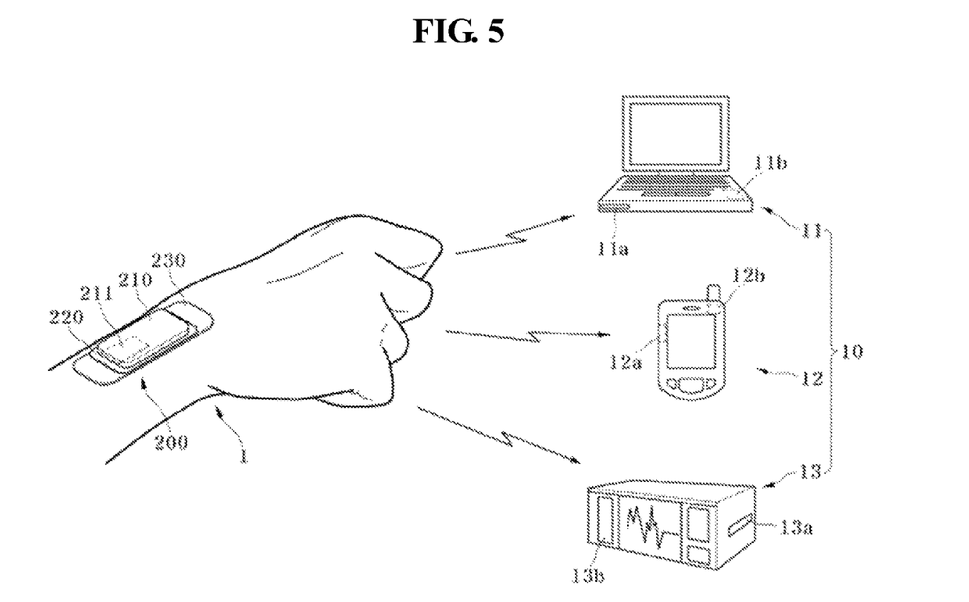
FIG. 5 is a drawing showing a configuration of a biological signal measuring apparatus including a detachable biological signal measuring pad according to a second embodiment of the present invention.

FIG. 5 is a drawing schematically showing a system configuration of a biological signal measuring apparatus according to a second embodiment of the present invention.

As shown in FIG. 5, the biological signal measuring apparatus of the present invention includes a detachable biological signal measuring pad 200 that is detachably adhered to a user's body such as a wrist 1 like a band-aid, and an analysis device 10 that receives and analyzes the biological signals measured in the measuring pad 200. That is, when the biological signal measuring pad 200 is attached to a user's skin, biological signals such as a pulse or a body temperature are measured and recorded in the memory card 211 mounted in the pad 200, the recorded information is analyzed which is transmitted to a computer 11 of the medical institution, a mobile phone such as a smart phone, or a dedicated terminal 13, and then transmitted to the user as useful information. Here, as an example, a case in which the measuring pad 200 is attached to the wrist 1 has been described, but the measuring pad 200 may be attached to the chest or the head, as necessary, and the measured biological signals encompass ECG waveforms, EEG waveforms, EMG waveforms, pulse waveforms, a body temperature, a blood sugar, and the like.

Accordingly, a user attaches the biological signal measuring pad 200 to an appropriate body region so as to measure biological signals, as necessary, while carrying the biological signal measuring pad 200 like a band-aid, and transmits the measured biological signals to the analysis device 10 to check his own health status and required measures.

As a method of transmitting the biological signals to the analysis device 10, both a method in which the memory card 211 mounted on the measuring pad 200 is pulled and directly inserted into card slots 11a, 12a, and 13a of the analysis device 10 to thereby load measured data, and a method in which the biological signals are transmitted to the communication modules 11b, 12b, and 13b of the analysis device 10 in a wireless manner using PAN, may be used.

Figure 6:
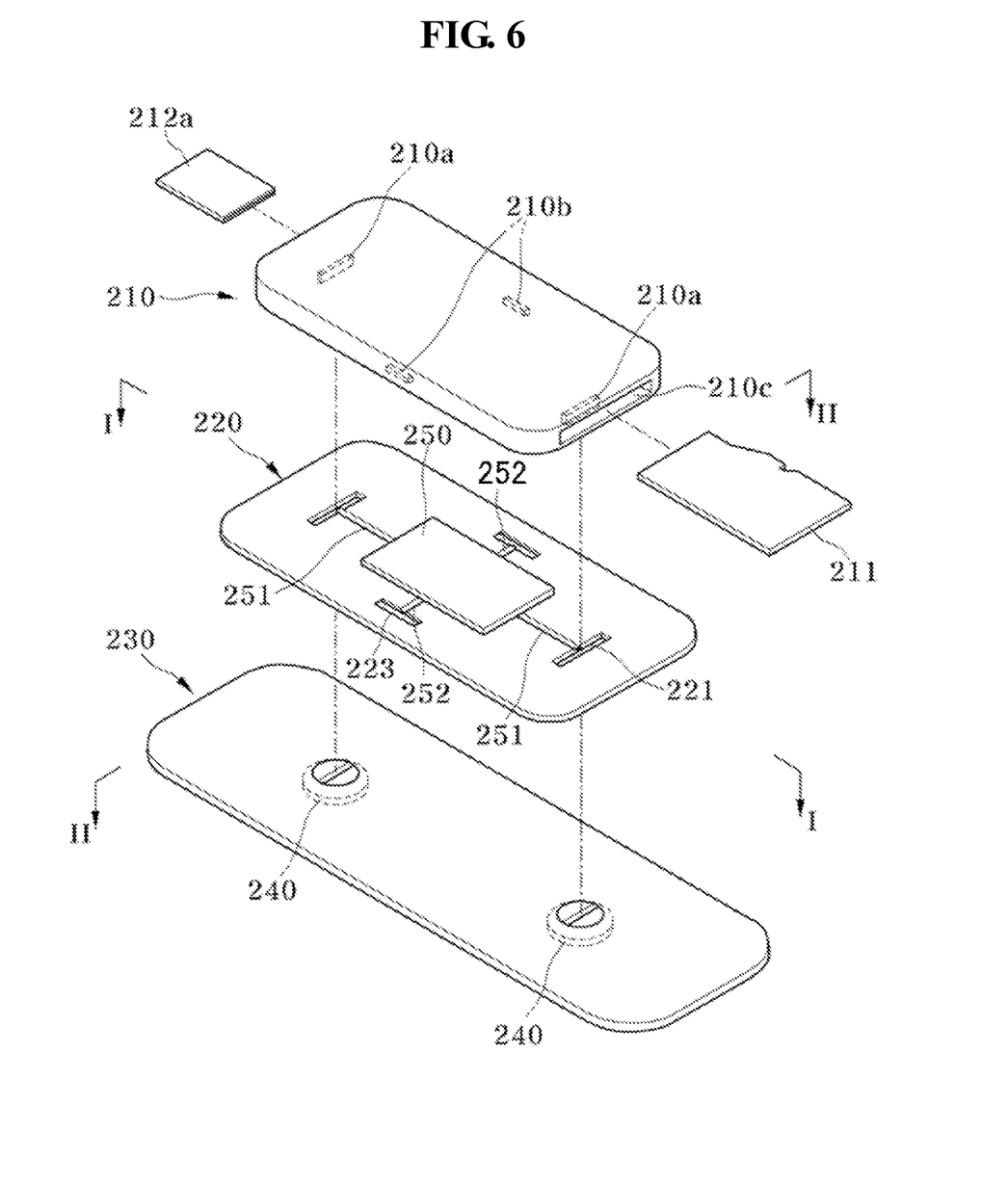
FIG. 6 is an exploded perspective view showing the detachable biological signal measuring pad shown in FIG. 5.
Figure 7:
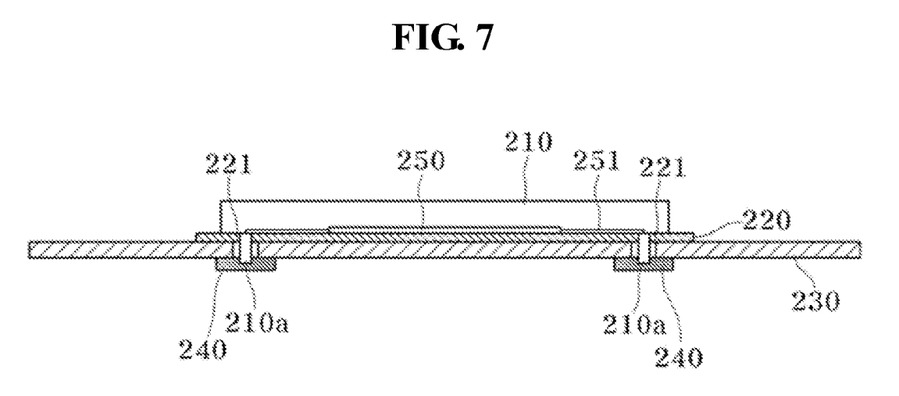
FIGS. 7 and 8 are cross-sectional views showing a coupling state of FIG. 6.
Figure 8:
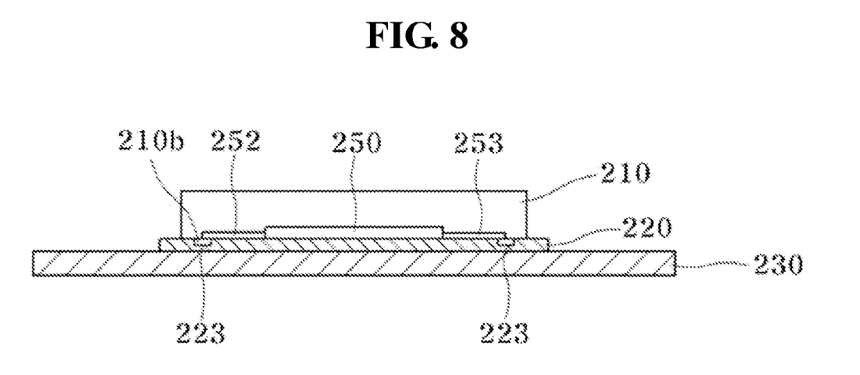
Figure 9:
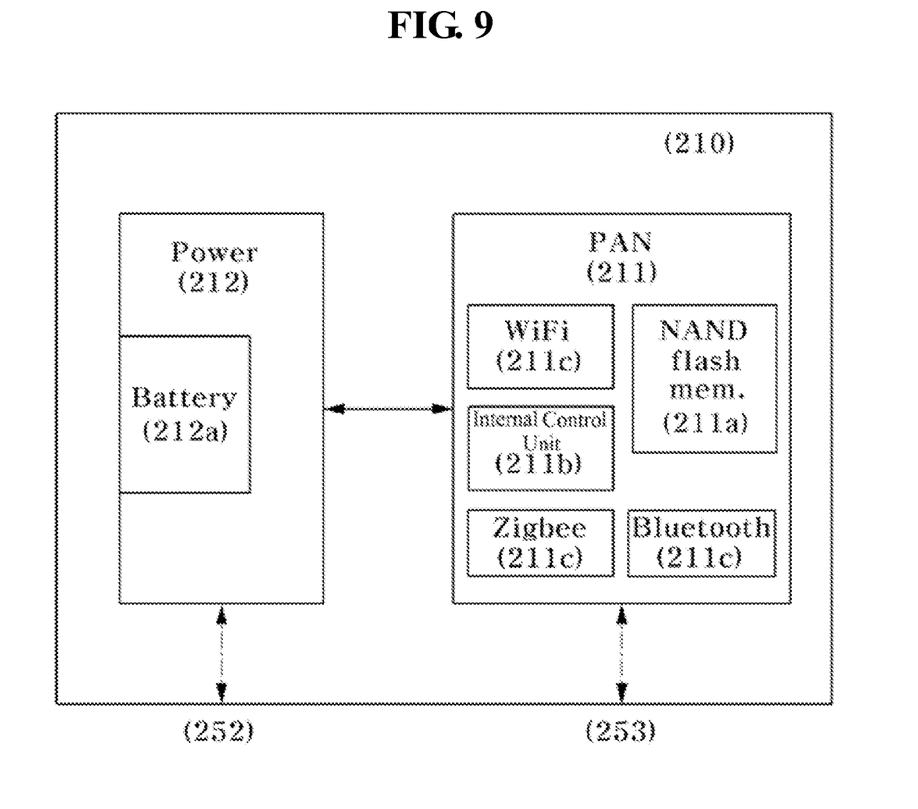
FIG. 9 is a drawing showing an internal configuration of a card module chip of the detachable biological signal measuring pad shown in FIG. 6.
Figure 10:
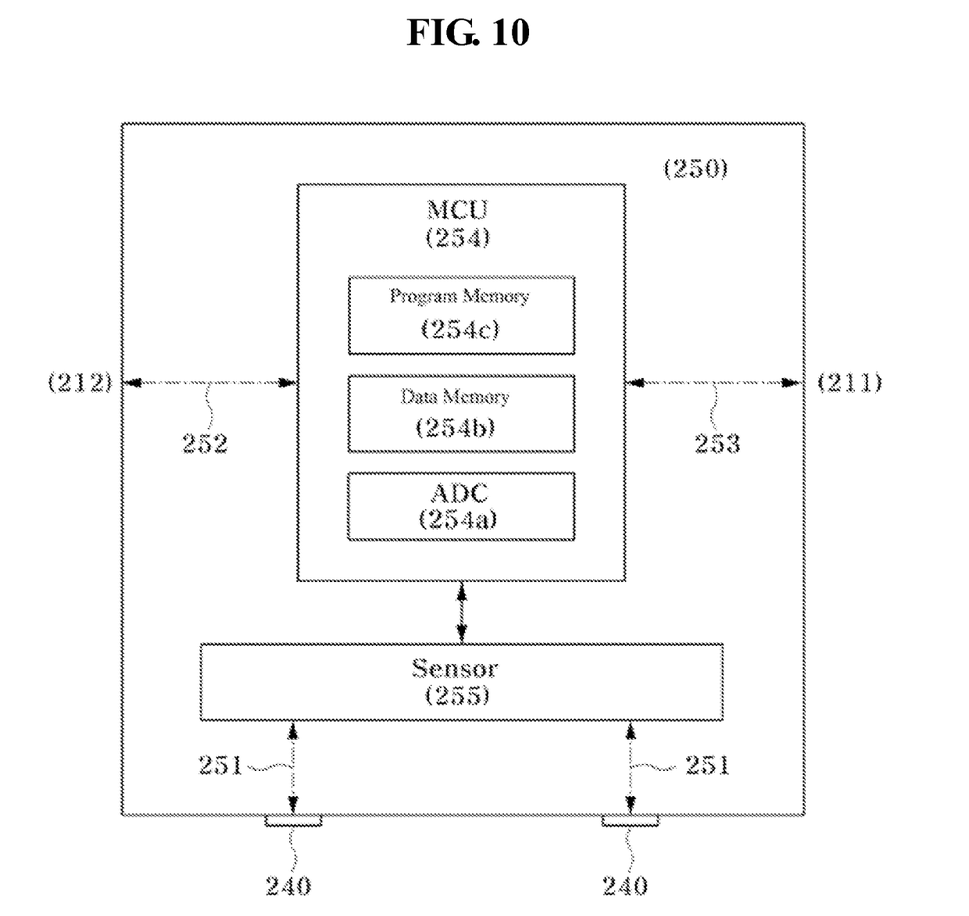
FIG. 10 is a drawing showing an internal configuration of a sensing module chip of the detachable biological signal measuring pad shown in FIG. 6.

Hereinafter, the biological signal measuring pad 200 according to an embodiment of the present invention which is configured so as to implement the above-described function will be described in detail. FIG. 6 is a drawing showing an exploded state of a structure of the biological signal measuring pad 200, and FIGS. 7 and 8 are drawings respectively showing a coupling state of the biological signal measuring pad 200. FIGS. 9 and 10 are drawings respectively showing an internal structure of a card module chip 210 and a sensing module 250 which are core components.

First, referring to FIGS. 6 to 8, the biological signal measuring pad 200 includes an adhesive pad main body 230 capable of attaching to skin, a module chip 210 in which a memory card 211 and a battery 212a are detachably inserted through a slot 210c, a connecting pad 220 interposed between the adhesive pad main body 230 and the card module chip 210, and a sensing module 250 provided on the connecting pad 220.

In the drawings, a bottom surface of the pad main body 230 is an adhesive surface attached to skin, and a pair of electrodes 240 for measuring biological signals is mounted on the adhesive surface. That is, when attaching the measuring pad 200 to the skin, the pair of electrodes 240 are brought into contact with the skin, and receive biological signals such as a pulse or a body temperature as electrical signals. Next, the pair of electrodes 240 are physically coupled with a connecting pin 210a of the module chip 210 through a connecting means provided in a connecting pad 220. Accordingly, the biological signals received through the electrode 240 are transmitted to the module chip through the connecting pin 210a. A reference numeral 221 indicates a plug groove constituting the connecting means for connecting the electrode 240 and the module chip 210 together with the connecting pin 210a. That is, the connecting pin 210a of the module chip 210 is connected to the electrode 240 provided on the pad main body 230 through the plug grove 221 of the connecting pad 220. Accordingly, the card module chip 210 and the connecting pad 220 are physically coupled with the electrode 240. In addition, the plug grooves 221 of the connecting pad 220 are electrically connected with the sensing module 250 provided on the connecting pad 220 through a wire 251. Accordingly, biological signals received through the electrode 240 are transmitted to the sensing module 250 through the connecting pin 210a. The pad main body 230 and the connecting pad 220 are coupled with each other using an adhesive. A configuration of the card module chip 210 and a signal processing process in the sensing module 250 will be described below with reference to FIGS. 9 and 10.

Preferably, the connecting pad may further include a signal connection means for electrically connecting the sensing module chip 250 and the card module chip 210. A reference numeral 223 indicates a signal connection groove constituting the signal connection means for physically connecting to the sensing module 250 and the connecting pad 220 and electrically connecting to the card module chip 210, together with the signal connection pin 210b. That is, the signal connection pin 210b of the card module chip 210 is connected to the sensing module 250 provided on the connecting pad 220 through the signal connection groove 223 of the connecting pad 220. Accordingly, the card module chip 210 and the sensing module 250 are electrically connected with each other.

Next, an internal configuration of the card module chip 210 will be described with reference to FIG. 9. As shown in FIG. 9, the card module chip 210 includes a memory card 211 for storing biological signals which are detected from the electrode 240 and amplified in the sensing module 250, and whose noise is removed, and a power supply unit 212 for supplying power. As described in FIG. 6, the memory card 211 and the battery 212a are detachably inserted in the card module chip 210 through the slot 210c, the battery 212a inserted in the card module chip 210 is mounted on the power supply unit 212, and power is supplied to the sensing module 250 through a wire 252. The memory card 211 receives biological signals from the sensing module 250. The memory card 211 includes a memory unit 211a for storing measured digital biological signals, a communication unit 211c for transmitting the stored biological signals to the outside, and an internal control unit 211b for controlling storage and transmission in accordance with a control of the card module chip 210. The internal control unit 211b may compress or encrypt data. The communication unit 211c may include zigbee, Bluetooth, WiFi, or the like, as PAN. Accordingly, the biological signal data stored in the memory unit 211a may be transmitted by communicating with the communication modules 11b, 12b, and 13b of the analysis device 10 through the communication unit 211c as described above. Alternatively, the biological signal data may be transmitted in such a manner that the memory card 211 itself is pulled out from the module chip 210, and then is loaded which is inserted into the card slots 11a, 12a, and 13a of the analysis device 10.

Next, an internal configuration of the sensing module chip 250 will be described with reference to FIG. 10. As shown in FIG. 10, the sensing module chip 250 includes a sensing unit 255 for amplifying biological signals from the electrode 240 and removing noise, and a microcomputer unit 254 for controlling the sensing module chip 250 by processing the biological signals input from the sensing unit 255 and storing the processed signals in the memory card 211 of the card module chip 210. The microcomputer unit 254 includes an AD converter 254a for converting biological signals received through the sensing unit 255 from analog signals to digital signals, a data memory 254b for storing the biological signals converted into the digital signals, and a program memory 254c for storing a program controlling the card module chip 210. Accordingly, analog biological signals received from the sensing unit 255 in accordance with a program stored in the program memory 254c are converted into digital signals through the AD converter 254a, stored in the data memory 254b, transmitted to the memory card 211 of the card module chip 210, and then stored in the memory unit 211a.

The biological signal measuring apparatus described as above may be utilized as follows.

First, as shown in FIG. 5, a user attaches the biological signal measuring pad 200 to an appropriate body region when wishing to measure his own health status while carrying the biological signal measuring pad 200. A variety of types of pads 200 used in ECG waveforms, EEG waveforms, EMG waveforms, pulse waveforms, a body temperature, a blood sugar, and the like, may be attached according to applications of the pad 200. Here, a case in which a user attaches the pad 100 to his own wrist 1 to measure a pulse waveform is assumed. Obviously, in this instance, the memory card 211 for data storage and communication and the battery 212a that is a power source should be mounted in the module chip 210. Before attaching the pad 200 to the body, a conductive gel may be attached to the electrode 240. In this manner, when attaching the pad 200 to the wrist 1, analog biological signals such as pulse waveforms are measured through the electrode 240, and the measured analog biological signals are transmitted to the sensing module chip 250 through the connecting pin 210a connected with the electrode 240. The analog signals transmitted into the module chip 250 are amplified in the sensing unit 255, converted into digital signals in the AD converter 254a, and then stored in the data memory 254b and the memory unit 211a of the memory card 211 of the card module chip 210. In this state, when the user wishes to check analyzed results by immediately transmitting the measured biological signals to the analysis device 10, data may be transmitted in such a manner that the communication unit 211c is connected with the communication modules 11a, 12a, and 13a of the analysis device 10 in a wireless manner. Although not shown in the drawings, a transmission button may be provided on one side of the card module chip 210, and the internal control unit 211b operates the communication unit 211c to thereby initiate wireless communication when a corresponding button is pushed by a user. Alternatively, a user pulls the memory card 211 out from the module chip 210, and directly mounts the memory card 211 in the analysis device 10 to thereby transmit data.

The analysis device 10 analyzes the transmitted biological signals, and informs diagnostic results suitable for the analyzed signals. When the pulse waveform measured by the user is in a normal range, the analysis device 10 informs a corresponding diagnostic result as normal, and when the pulse waveform is in an abnormal range such as bradycardia or pyknocardia, the analysis device 10 informs required measures such as recommending diagnosis of a corresponding health status and consultation with experts, or the like. Then, the user may well manage his health status by appropriately performing corresponding measures.

Therefore, by utilizing the detachable biological signal measuring pad and apparatus, a user may conveniently measure his own health status anytime and anywhere, and communicate with the analysis device by loading the detachable memory card in the analysis device or using wireless communication, and therefore the measured results are rapidly utilized. As a result, rapid measuring and utilization of the biological signals are achieved to thereby realize a healthy society.

Meanwhile, in the biological signal measuring pad according to the second embodiment of the present invention, it should be noted that the memory card and the power supply unit may be attached and detached to and from the card module chip, and the sensing unit may be mounted in the sensing module chip. In this manner, when the sensing unit is mounted in separate module chips, a user may select a sensing unit having a sensing function with respect to his suspected disease. That is, the sensing unit may be manufactured so as to have only its own unique sensing function. Therefore, sizes of the card module chip and the sensing module chip may be reduced, and only one sensing function is driven to thereby reduce power consumption. By the reduction in size and power consumption, the detachable biological signal measuring pad according to the present invention may be more easily carried.

The present invention has been described with reference to the embodiments shown in the drawings, but this is merely an example, and it will be apparent to those skilled in the art that various modifications can be made to the above-described exemplary embodiments of the present invention without departing from the spirit or scope of the invention.

For example, in the present specification, the detachable biological signal measuring pad including two electrodes has been described. However, the present invention may be implemented in the detachable biological signal measuring pad having one or at least three electrodes. Each electrode may be used for different types of measuring biological signals.

In addition, in the present specification, an example in which the connecting means and the signal connection means are separately implemented has been described, but an integrated type of the connecting means and the signal connection means may be implemented. For example, the connecting means may include at least three wires, the electrode may be connected to the sensing module chip without being connected to the card module chip, and the power supply unit and the memory card of the card module chip may be connected only to the sensing module chip without being connected to the electrode.

In addition, in the present specification, an example in which the memory card is detachable has been described, but a built-in memory incapable of being attached and detached may be used instead of the memory card. In this case, the module chip may be directly connected to the analysis device to thereby transmit data from the built-in memory to the analysis device.

In addition, in the present specification, an example in which the electrode directly contacts the skin has been described, but a transducer for converting chemical or physical values into electrical signals may be provided between the electrode and the skin. The transducer may be electrically connected to the electrode, and fixed in the pad main body. As an example, the transducer may be a blood sugar sensor for transmitting electrical signals corresponding to blood sugar values to the electrode. In this case, the blood sugar sensor may include a microneedle array for forming a fine hole in the skin, and a blood sugar analysis unit for forming electrical signals corresponding to a blood sugar value from blood transmitted through the microneedle array.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

The invention claimed is:

1. A detachable biological signal measuring pad, comprising:
   an adhesive pad main body for detachably adhering to a human body;
   a biological signal detecting electrode provided on an adhesive surface of the main body and detecting a biological signal generated from the human body;
   a module chip including a memory card, and mounted on the main body so as to be connected with the electrode, and storing biological signals measured in the electrode, and provided on a surface of the main body opposite to the adhesive surface, the module chip further including a connecting pin protruding from the module chip; and a connecting pad provided between the electrode of the main body and the module chip, and having a plug groove through which the connecting pin penetrates the connecting pad to make a direct electrical connection with the electrode, wherein the connecting pin is directly connected to the electrode, and the module chip is forcibly coupled to the electrode by the connecting pin, wherein the connecting pad further comprises a first adhesive member disposed on a first side of the connecting pad to couple the connecting pad with the module chip, wherein the main body and the connecting pad are coupled with each other by an adhesive.

2. The detachable biological signal measuring pad of claim 1, further comprising a second adhesive member provided below the module chip to couple the module chip with the connecting pad.

3. The detachable biological signal measuring pad of claim 1, wherein the memory card is detachably coupled to the module chip.

4. The detachable biological signal measuring pad of claim 3, wherein the memory card includes a memory unit for storing the measured biological signals, a communication unit for transmitting the stored biological signals to the outside, and an internal control unit for controlling storage and transmission in accordance with a control of the module chip.

5. The detachable biological signal measuring pad of claim 1, wherein the module chip includes a sensing unit for amplifying the biological signals from the electrode and removing noise, a microcomputer unit for controlling the module chip by processing the biological signals input from the sensing unit to store the processed biological signals in the memory card, and a power supply unit for supplying power to the module chip.

6. The detachable biological signal measuring pad of claim 5, wherein the microcomputer unit includes an AD converter for converting analog signals input from the sensing unit into digital signals, a data memory for storing biological signals converted into the digital signals, and a program memory for storing a program controlling the module chip.

7. A biological signal measuring apparatus comprising:

a detachable biological signal measuring pad including an adhesive pad main body for detachably adhering to a human body, a biological signal detecting electrode provided on an adhesive surface of the main body and detecting a biological signal generated by the human body, and a module chip including a memory card, and mounted on the main body so as to be connected with the electrode and storing biological signals measured in the electrode; and an analysis device receiving and analyzing the biological signals stored in the memory card, wherein the module chip further includes a connecting pin protruding from the module chip, wherein the detachable biological signal measuring pad further comprises:

a connecting pad provided between the electrode of the main body and the module chip, and having a plug groove through which the connecting pin penetrates the connecting pad to make a direct electrical connection with the electrode, wherein the connecting pin is directly connected to the electrode, and the module chip is forcibly coupled to the electrode by the connecting pin, wherein the connecting pad further comprises a first adhesive member disposed on a first side of the connecting pad to couple the connecting pad with the module chip, wherein the main body and the connecting pad are coupled with each other by an adhesive.

8. The biological signal measuring apparatus of claim 7, wherein the analysis device includes any one of a terminal for the memory card, a mobile phone, and a computer which has a card slot through which the memory card separable from the module chip is able to be inserted.

9. The biological signal measuring apparatus of claim 8, wherein a communication module capable of communicating with the memory card in a wireless manner is provided in the analysis device.

* * * * *